United States Patent [19]

Miller et al.

[11] Patent Number: 4,551,739

[45] Date of Patent: Nov. 5, 1985

[54] RECORD MEMBER

[75] Inventors: Robert E. Miller; Steven L. Vervacke, both of Appleton, Wis.

[73] Assignee: Appleton Papers Inc., Appleton, Wis.

[21] Appl. No.: 612,957

[22] Filed: May 23, 1984

[51] Int. Cl.[4] .................. B41M 5/16; B41M 5/22
[52] U.S. Cl. ............................. 346/216; 346/219; 346/225; 427/150
[58] Field of Search ............ 346/216, 217, 225, 214, 346/215, 219; 427/150–152

[56] References Cited

U.S. PATENT DOCUMENTS 4,436,783  3/1984  Okumura et al. ............... 428/913
4,467,339  8/1984  Asami et al. .................... 346/216

FOREIGN PATENT DOCUMENTS 0155059  12/1979  Japan ............................. 346/217

*Primary Examiner*—Bruce H. Hess
*Attorney, Agent, or Firm*—E. Frank McKinney; Paul S. Phillips, Jr.

[57] ABSTRACT

A record member comprising a developer composition comprising 2,2-bis(4-hydroxyphenyl)-5-methylhexane is disclosed. This compound is particularly useful as a color developer for basic chromogenic material.

10 Claims, No Drawings

RECORD MEMBER

This invention relates to the production of novel record material. More specifically, the invention involves sensitized record sheet material useful in developing dark-colored marks on contact with colorless solutions of basic chromogenic material (also called color formers). Such sheet material includes color developer material generally in the form of a coating on at least one sheet surface. The coating of color developer material serves as a receiving surface for colorless, liquid solutions of color formers which react, on contact, with the color developer material to produce the dark-colored marks.

Pressure-sensitive carbonless copy paper of the transfer type consists of multiple cooperating superimposed plies in the form of sheets of paper which have coated, on one surface of one such ply, pressure-rupturable microcapsules containing a solution of one or more color formers (hereinafter referred to as a CB sheet) for transfer to a second ply carrying a coating comprising one or more color developers (hereinafter referred to as a CF sheet). To the uncoated side of the CF sheet can also be applied pressure-rupturable microcapsules containing a solution of color formers resulting in a pressure-sensitive sheet which is coated on both the front and back sides (hereinafter referred to as a CFB sheet). When said plies are superimposed, one on the other, in such manner that the microcapsules of one ply are in proximity with the color developers of the second ply, the application of pressure, as by typewriter, sufficient to rupture the microcapsules, releases the solution of color former and transfers color former solution to the CF sheet resulting in image formation through reaction of the color former with the color developer. Such transfer systems and their preparation are disclosed in U.S. Pat. No. 2,730,456.

The use of certain biphenols as color developers in pressure-sensitive carbonless copy paper is disclosed in U.S. Pat. No. 3,244,550. Application Ser. No. 478,199, filed Mar. 24, 1983 and application Ser. No. 401,678, filed July 26, 1982, now abandoned, both in the name of Kenneth D. Glanz, disclose thermally-responsive record material comprising phenolic developers including 2,2-bis(4-hydroxyphenyl)-5-methylhexane. U.S. Pat. No. 4,408,781 discloses a recording material comprising an acid-treated clay, a polyalkylene oxide compound and a bisphenol compound.

Although certain biphenol compounds have been suggested for use as color developers in pressure-sensitive carbonless copy paper, the compounds suggested have failed to overcome certain existing problems in carbonless copy paper or have proven to have defects of their own which make them unattractive as color developers in commercial carbonless copy paper systems. The greatest single problem of many of the biphenol color developers previously suggested has been their failure to provide an adequately intense image under conditions of use in carbonless copy paper systems. The second greatest defect of these suggested biphenol developers has been that, even if they were utilized in carbonless copy paper systems in such a manner that an adequately intense image was obtained initially, this ability to continue to provide an adequately intense print was seriously reduced merely upon the natural aging of the coated sheet (hereinafter referred to as CF decline).

Among the existing problems in carbonless copy systems which the previously-suggested biphenol developers have failed to overcome is speed of image formation.

It is therefore an object of the present invention to provide a record member having improved image intensity, both initially and upon aging.

Another object of the present invention is to provide a record member having improved speed of image formation.

Yet another object of the present invention is to provide a record member comprising a substrate and a developer composition comprising 2,2-bis(4-hydroxypenyl)-5-methylhexane.

In accordance with the present invention, it has been found that these and other objectives may be attained by employing a CF sheet which comprises a substrate coated with a developer composition comprising 2,2-bis(4-hydroxyphenyl)-5-methylhexane.

The developer composition comprising 2,2-bis(4-hydroxyphenyl)-5-methylhexane can be utilized in either a transfer carbonless copy paper system as disclosed hereinbefore or in a self-contained carbonless copy paper system such as disclosed in U.S. Pat. Nos. 2,730,457 and 4,167,346. Many of both types of carbonless copy paper systems are exemplified in U.S. Pat. No. 3,672,935. Of the many possible arrangements of the mark-forming components in the transfer type of carbonless copy paper system, the most commonly employed is the one wherein the developer composition includes the color developer, one or more pigment materials and one or more binders. These compositions are then applied in the form of a wet slurry to the surface of what becomes the underlying ply (the CF sheet) in the carbonless copy paper system. Such CF sheet color developer composition coatings are disclosed in U.S. Pat. Nos. 3,455,721; 3,732,120; 4,166,644; and 4,188,456. Another useful arrangement of the developer composition is to prepare a sensitizing solution of the developer material and apply the solution to the nap fibers of sheet paper as disclosed in U.S. Pat. No. 3,466,184. A suitable alternative is to apply such a sensitizing solution of developer material to a base-coated sheet wherein the base coating comprises a pigment material. Examples of such pigment material include calcium carbonate, kaolin clay, calcined kaolin clay, etc. and mixtures thereof.

Examples of eligible color formers for use with the color developer composition of the present invention, to develop dark colored marks on contact, include, but are not limited to, Crystal Violet Lactone [3,3-bis(4-dimethylaminophenyl)-6-dimethylaminophthalide (U.S. Pat. No Re. 23,024)]; phenyl-, indol-, pyrrol-, and carbazol-substituted phthalides (for example, in U.S. Pat. Nos. 3,491,111; 3,491,112; 3,491,116; 3,509,174); nitro-; amino-, amido-, sulfon amido-, aminobenzylidene-, halo-, anilino-substituted fluorans (for example, in U.S. Pat. Nos. 3,624,107; 3,627,787; 3,641,011; 3,642,828; 3,681,390); spirodipyrans (U.S. Pat. No. 3,971,808); and pyridine and pyrazine compounds (for example, in U.S. Pat. Nos. 3,775,424 and 3,853,869). Other specifically eligible chromogenic compounds, not limiting the invention in any way, are: 3-diethylamino-6-methyl-7-anilino-fluoran (U.S. Pat. No. 3,681,390); 7-(1-ethyl-2-methylindol-3-yl)-7-(4-diethylamino-2-ethoxyphenyl)-5,7-dihydrofuro[3,4-b]pyridin-5-one (U.S. Pat. No. 4,246,318); 3-diethylamino-7-(2-chloroanilino)fluoran (U.S. Pat. No. 3,920,510); 3-(N-methylcyclohexylamino)-6-methyl-7-anilinofluoran (U.S. Pat. No. 3,959,571); 7-(1-octyl-2-methylindol-3-yl)-7-(4-diethylamino-2-ethoxyphenyl)-5,7-dihydrofuro[3,4-b]pyridin-5-one; 3-diethylamino-7,8-benzofluoran; 3,3-bis(1-ethyl-2-methylindol-3-yl)phthalide; 3-diethylamino-7-anilinofluoran; 3-diethylamino-7-benzylaminofluoran; 3'-phenyl-7-dibenzylamino-2,2'-spiro-di[2H-1-benzopyran]; and mixtures of any two or more of the above.

The following examples are given merely as illustrative of the present invention and are not to be considered as limiting. All percentages and parts throughout the application are by weight unless otherwise specified.

EXAMPLE 1

Preparation of 2,2-bis(4-hydroxyphenyl)-5-methylhexane

A mixture of 150 grams of phenol, 36 grams of 5-methyl-2-hexanone and 0.1 ml. of octanethiol was heated to 45°–50° C., HCl gas was bubbled through the mixture, 100 ml. of concentrated hydrochloric acid was added, the temperature of the mixture was lowered to 12°–15° C. and the addition of the HCl gas was continued for 5–10 minutes to assure saturation. The mixture was sealed in a Parr bomb and the bomb was charged with gaseous nitrogen to 250 pounds per square inch. The reaction mixture was heated, with stirring, to about 70° C. over a period of about two hours and the temperature and stirring were maintained for an additional 16–18 hours. Toluene was added to the reaction mixture and the aqueous layer was removed by means of a separatory funnel. The toluene layer was washed once with water, washed repeatedly with a saturated sodium bicarbonate solution until the toluene layer was neutralized and then washed with water three more times to remove the excess sodium bicarbonate. The toluene layer was steam distilled to remove excess phenol, the excess water was decanted and the remaining water was removed by azeotropic distillation using toluene. A 20 gram portion of the 36 grams of crude product was recrystallized from a benzene-heptane mixture yielding 10 grams of the title compound which was dried at about 95° C. for about 5 hours.

EXAMPLE 2

Preparation of 2,2-bis(4-hydroxyphenyl)butane

In a procedure substantially like that of Example 1, a mixture of 60 grams of phenol and 8 grams of 2-butanone was reacted in the presence of 1 ml. of mercaptoacetic acid (a catalyst used in place of the octanethiol of Example 1) and 40 ml. of concentrated hydrochloric acid. The Parr bomb and gaseous nitrogen were not used in this procedure. The reaction temperature was about 55° C. The crude reaction product was recrystallized from benzene to yield 5.2 grams of the title compound, which was dried overnight at about 95° C.

The products of Example 1 and Example 2 were individually formulated into mixtures of the following composition:

| Component | Parts, wet |
| --- | --- |
| Bisphenol Compound | 5 |
| Kaolin Clay slurry (68% solids) | 70 |
| 10% polyvinyl alcohol in water | 25 |
| Water | 75 |

The mixture was dispersed in a Waring blender for five minutes at high speed. The dispersion was applied to a paper base with a No. 12 wire-wound coating rod and dried at room temperature. The resulting CF sheets were tested in a Typewriter Intensity (TI) test with CB sheets comprising a coating of the composition listed in Table 1 applied as an 18% solids dispersion to a paper base using a No. 12 wire-wound coating rod.

TABLE 1

| Material | % Dry |
| --- | --- |
| Microcapsules | 74.1% |
| Corn Starch Binder | 7.4% |
| Wheat Starch Particles | 18.5% |

The microcapsules employed contained the color former solution of Table 2 within capsule walls comprising synthetic resins produced by polymerization methods utilizing initial condensates as taught in U.S Pat. No. 4,100,103.

TABLE 2

| Material | Parts |
| --- | --- |
| 7-(1-ethyl-2-methylindol-3-yl)-7-(4-diethylamino-2-ethoxyphenyl)-5,7-dihydrofuro[3,4-b]pyridin-5-one | 1.70 |
| $C_{10}$–$C_{13}$ alkylbenzene | 78.64 |
| sec-butylbiphenyl | 19.66 |

In the TI test a standard pattern is typed on a coated side-to-coated side CB-CF pair. The image intensity is measured initially and after 20 minutes and 8 hours development, respectively, and reported as color difference.

The Hunter Tristimulus Colorimeter wa used in these Examples to measure color difference, a quantitative representation of the ease of visual differentiation between the colors of two specimens. The Hunter Tristimulus Colorimeter is a direct-reading L, a, b instrument. L, a, b is a surface color scale (in which L represents lightness, a represents redness-greenness and b represents yellowness-blueness) and is related to the CIE tristimulus values, X, Y and Z, as follows:

$$L = 10Y^{\frac{1}{2}}$$

$$a = \frac{17.5[(X/0.98041) - Y]}{Y^{\frac{1}{2}}}$$

$$b = \frac{7.0[Y - Z/1.18103)]}{Y^{\frac{1}{2}}}$$

The magnitude of total color difference is represented by a single number $\Delta E$ and is related to L, a, b values as follows:

$$\Delta E = [(\Delta L)^2 + (\Delta a)^2 + (\Delta b)^2]^{\frac{1}{2}}$$

where
$\Delta L = L_1 - L_o$
$\Delta a = a_1 - a_o$
$\Delta b = b_1 - b_o$
$L_1, a_1, b_1$ = object for which color difference is to be determined.
$L_o, a_o, b_o$ = reference standard.

The above-described color scales and color difference measurements are described fully in Hunter, R.S.

"The Measurement of Appearance", John Wiley & Sons, New York, 1975.

In Table 3 are listed the color difference values obtained for each of the Examples at each of the measurement intervals.

TABLE 3

| Example | ΔE at Indicated Measurement Intervals* | | |
|---|---|---|---|
| | Initial | 20 Min. | 8 Hr. |
| 1 | 18.32 | 26.81 | 31.47 |
| 2 | 12.81 | 18.13 | 26.78 |

*An average of duplicate determinations for each Example.

Since ΔE is proportional to the amount of color present, it can readily be seen that the color developer of the present invention, 2,2-bis(4-hydroxyphenyl)-5-methylhexane, produces, initially and at the other two measurement periods, substantially more color than the reference compound, 2,2-bis(4-hydroxyphenyl)butane. The compound of the present invention produced 143% (initially), 148% (20 minutes) and 118% (8 hours) of the amount of color produced by the reference compound at the same reading periods. Thus, the compound of the present invention produces surprisingly greater image intensity than the reference color developer. Also, the compound of the present invention produced 58% and 85%, initially and at 20 minutes, respectively, of the 8 hour print intensity. The reference color developer produced 48% and 68% initially and at 20 minutes, respectively, of the 8 hour print intensity. Thus, the compound of the present invention produces surprisingly improved speed of image formation when compared to that of the reference color developer.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A record member comprising a substrate and a developer composition comprising 2,2-bis(4-hydroxyphenyl)-5-methylhexane.

2. The record member of claim 1 which further comprises one or more pigment materials.

3. The record member of claim 2 wherein the pigment material is selected from the group consisting of kaolin clay, calcium carbonate, calcined kaolin clay, zinc oxide, talc and urea-formaldehyde agglomerated resin pigment.

4. The record member of claim 3 wherein the pigment material is kaolin clay.

5. The record member of claim 4 which further comprises calcined kaolin clay.

6. A pressure-sensitive record unit comprising:
    (a) support sheet material;
    (b) mark-forming components, and a pressure-releasable liquid organic solvent for both said mark-forming components arranged in contiguous juxtaposition and supported by said sheet material;
    (c) at least one of the mark-forming components being maintained in isolation from other mark-forming component(s);
    (d) said mark-forming component comprising at least one basic chromogenic material and 2,2-bis(4-hydroxyphenyl)-5-methylhexane.

7. The record unit of claim 6 which further comprises one or more pigment materials.

8. The record unit of claim 7 wherein the pigment material is selected from the group consisting of kaolin clay, calcium carbonate, calcined kaolin clay, zinc oxide, talc and urea-formaldehyde agglomerated resin pigment.

9. The record unit of claim 8 wherein the pigment material is kaolin clay.

10. The record unit of claim 9 which further comprises calcined kaolin clay.

* * * * *